United States Patent

Galambos et al.

Patent Number: 4,740,523

Date of Patent: Apr. 26, 1988

[54] INTERFURANYLENE PROSTACYCLINS

[75] Inventors: Géza Galambos; József Ivanics; György Dorman; Károly Kánay; István Tömösközy; Gábor Kovács; István Stadler; Péter Körmöczi; Pál Hadházy; Sándor Virág; Miklós Kiss, all of Budapest, Hungary

[73] Assignee: Chinoin Gyogyszer es Vegyeszeti Termekek Gyar Rt, Budapest, Hungary

[21] Appl. No.: 820,434

[22] Filed: Jan. 17, 1986

[30] Foreign Application Priority Data

Jan. 17, 1985 [HU] Hungary ................. 195/85

[51] Int. Cl.$^4$ ................. A61K 31/35; C07D 311/00
[52] U.S. Cl. ................. 514/456; 549/396; 549/214
[58] Field of Search ................. 549/396, 214; 514/456

[56] References Cited

U.S. PATENT DOCUMENTS 4,337,203  6/1982  Axen et al. ................. 549/396

Primary Examiner—Nicky Chan
Attorney, Agent, or Firm—Karl F. Ross; Herbert Dubno; Jonathan Myers

[57] ABSTRACT

The invention relates to novel interfuranylene-prostacyclin derivatives of the general formula (I)

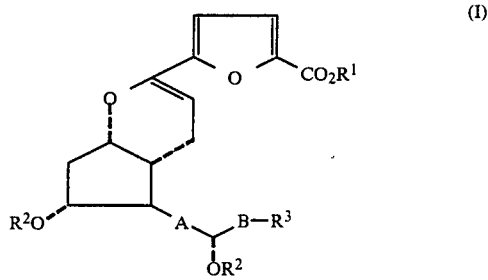

wherein
$R^1$ stands for hydrogen or a straight or branched chain $C_{1-6}$ alkyl group, an inorganic cation or for the protonated form of a base containing an amino group;
$R^2$ stands for hydrogen, a $C_{1-4}$ alkanoyl or benzoyl group, a monosubstituted benzoyl, trialkylsilyl or an alkoxyalkyl group;
$R^3$ stands for a straight or branched chain $C_{1-6}$ alkyl group, a phenyl group optionally substituted by halogen or by a $C_{1-4}$ alkyl group, a heteroaryl group optionally substituted by halogen or by a $C_{1-4}$ alkyl group or a cycloalkyl group;
A stands for an ethylene or for a cis- or trans-vinylene or —C≡C— group;
B means a chemical bond, a —CHR$^5$—, —CHR$^5$—CH$_2$— or a —CH$_2$—O— group: and
$R^5$ means hydrogen or a $C_{1-4}$ alkyl group.

The compounds of the formula (I) can be used therapeutically as platelet aggregation inhibiting, anti-thrombotic, hypotensive and anti-antherosclerotic agents; they are much more stable than the natural prostacyclin derivatives.

11 Claims, No Drawings

INTERFURANYLENE PROSTACYCLINS

FIELD OF THE INVENTION

The invention relates to novel interfuranylene-prostacyclin derivatives having a therapeutically useful biological activity. More particularly, the invention relates to new racemic and optically active interfuranylene-prostacyclin derivatives of the formula (I)

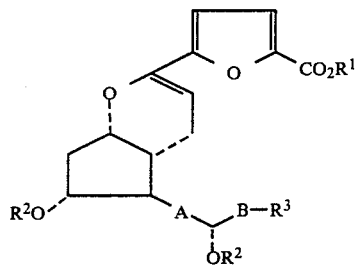

(I)

wherein $R^1$ is hydrogen or a straight or branched chain $C_{1-6}$ alkyl group, an inorganic cation or the protonated form of a base containing an amino group;

$R^2$ is hydrogen, a $C_{1-4}$ alkanoyl or benzoyl group, a monosubstituted benzoyl, trialkylsilyl or an alkoxyalkyl group;

$R^3$ is a straight or branched chain $C_{1-6}$ alkyl group, a phenyl group optionally substituted by halogen or by a $C_{1-4}$ alkyl group, a heteroaryl group optionally substituted by halogen or by a $C_{1-4}$ alkyl group or a cycloalkyl group;

A is an ethylene or a cis- or trans-vinylene or a —C≡C— group;

B means a chemical bond, a —CHR$^5$—, —CH-R$^5$—CH$_2$— or a —CH$_2$—O— group; and $R^5$ means hydrogen or a $C_{1-4}$ alkyl group, as well as to pharmaceutical compositions containing these compounds.

According to an other aspect of the invention, there is provided a process for the preparation of the new compounds of the formula (I), which comprises a. reacting a compound of the formula (III)

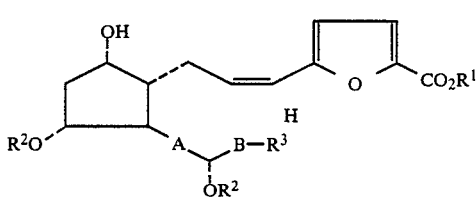

(III)

wherein $R^1$, $R^2$, $R^3$, A, B and $R^5$ are as defined above with a compound of the formula

E—X wherein E is halogen, an acid amide group or an acid imide group and X means halogen, and treating the resulting compound of the formula (IIa)

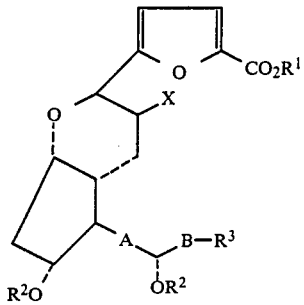

(IIa)

wherein $R^1$, $R^2$, $R^3$, A, B and X are as defined above, with a base; or b. reacting a compound of the formula (III), wherein $R^1$, $R^2$, $R^3$, A and B are as defined above, with a compound of the formula

F—Y wherein Y stands for an $R^6$-Se-group—where $R^6$ means a phenyl group optionally substituted by halogen or by a $C_{1-4}$ alkyl group—and F means halogen or a $C_{1-4}$ acyl group, and treating the resulting compound of the formula (IIb)

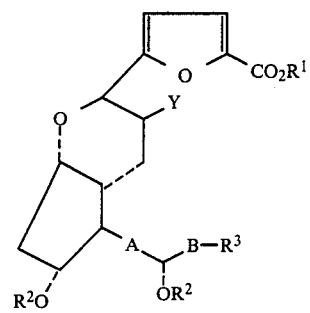

(IIb)

wherein $R^1$, $R^2$, $R^3$, A, B and Y are as defined above, with an oxidizing agent; or c. reacting a compound of the formula (V)

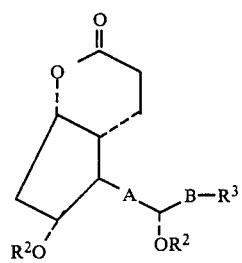

(V)

wherein $R^2$, $R^3$, A and B are as defined above, in the presence of a base with a compound of the formula (VI)

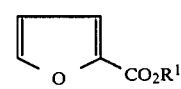

(VI)

wherein $R^1$ is as defined above, and heating the resulting ketone derivative of the formula (IV)

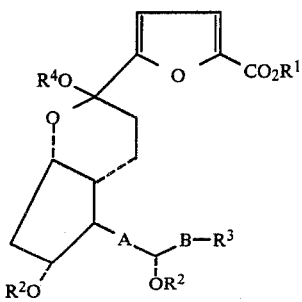

(IV)

wherein $R^1$, $R^2$, $R^3$, A and B are as defined above, and $R^4$ means hydrogen or a $C_{1-4}$ alkyl group, in the presence of an acid catalyst.

BACKGROUND OF THE INVENTION

The compounds of the formula (I) of the invention can be considered as analogs of prostacyclin ($PGI_2$), a physiologically very important natural substance, which are stable and possess a selective pharmacological action.

Prostacyclin ($PGI_2$) as a metabolite of arachidonic acid, which is wide-spread in mammalian organisms, was discovered in 1976. This substance possesses a number of therapeutically valuable biological effects: e.g. inhibits the aggregation of the blood platelets, lowers the blood pressure, dilatates the airways and diminishes the gastric juice secretion. In addition, prostacyclin shows a cyto-protective action in various organs, e.g. in the stomach, liver, heart and kidney. This means that the destructive consequences of various organ-damaging effects can be prevented or remedied by prostacyclin.

A large number of review articles have been published on the above-mentioned advantageous pharmacologic effects of prostacyclin (see e.g. Flohé et al.: Arnzeimittelforschung 33, 1240 (1983); S. Moncada and J. R. Vane: J. Med. Chem. 23, 591 (1980); W. Bartman et al.: Angewandte Chemie, Int. Ed. Engl. 21, 751 (1982); R. F. Newton et al.: Synthesis 1984, 449).

Today, the advantageous pharmacological actions of prostacyclin are also utilized clinically. The sodium salt has been commercialized by the Wellcome company under the trade name Flolan and by the Upjohn company under the trade name Cycloprostin in 1983 (Drugs of Today 19, 605 (1983)) for cardiopulmonary bypass proceses, perfusion in the course of liver deficiency and kidney haemolysis as areas of indication.

However, severe problems with the use of prostacyclin are induced by the extraordinary unstability of this substance (A. J. Kresge et al.: J. Chem. Soc. Chem. Comm. 1979, 129). The most sensitive moiety of the molecule is the ethanolether functional group. The main principles of the chemical and biological stabilization of the molecule are reported in the above-cited review articles.

DESCRIPTION OF THE INVENTION

The interfuranylene prostacyclin analogs of the formula (I) of our invention are much more stable compounds than natural prostacyclin. The compounds of the invention are stabilized in a manner hitherto not described in the literature. Their stability is based on their novel chemical structure. The upper ring of the compounds of the invention contains six members instead of five members, which is different from the structure of the natural prostacyclins. An unusual endocyclin enolether function is provided in this ring which is stabilized by the aromatic ring built into the upper chain. This aromatic ring exerts its effect through the delocalization of the electron system.

Surprisingly, the compounds of the formula (I) stabilized in this novel way show a spectrum of activities characteristic of the natural prostacyclin ($PGI_2$) in addition to a substantially higher stability and more selective mode of action. The compounds of the formula (I) can be prepared by using the above-described processes (a), (b) and (c), the preferable embodiments of which are reported below in detail.

a. A compound of the formula (III) is reacted with a halogenating agent of the formula E—X at a temperature from −20° C. to 100° C., preferably at room temperature. This reaction is carried out in an organic solvent such as an ether-type solvent, e.g. ethyl ether, tetrahydrofuran, dioxane; or in halogenated hydrocarbons, such as dichloromethane, chloroform, carbon tetrachloride or the like; or in polar aprotic solvents, such as acetonitrile or the like; or in alcohols, such as methanol, ethanol or the like; or in aromatic solvents, such as benzene, toluene or the like in the presence of or without an inorganic base, preferably in the presence of an alkali carbonate, such as sodium or potassium carbonate; or in the presence of an alkali hydrogen carbonate, such as sodium hydrogen carbonate.

A preferred embodiment of this reaction step comprises using N-bromosuccinimide as an E—X reagent dichloromethane as solvent and carrying out the reaction at room temperature without the presence of any base.

Subsequently, the resulting compounds of the formula (II) are transformed to the interfuranylene-prostacyclin derivatives of the formula (I) by eliminating a H—X molecule—wherein H stands for hydrogen and X means halogen—by using an organic or inorganic base in or without a solvent. This elimination reaction is performed at a temperature between 0° C. and 200° C., preferably at 80° to 120° C. As an organic base, it is preferred to use an amidine-type base, such as diazabicycloundecene (DBU) or diazabicyclononene (DBN) or the like, or a tertiary amine, such as triethylamine; or an aromatic base, such as pyridine alkali alkoxides, such as sodium methoxide, sodium ehtoxide, potassium tertiary-butoxide or the like. Inorganic bases, such as alkali hydroxides, e.g. potassium or sodium hydroxide can also preferably be used. As solvents, inorganic liquids, such as water, organic solvents, such as alcohols e.g. preferably methanol or ethanol or the like, or aromatic solvents, such as benzene and toluene, or polar aprotic solvents, such as dimethyl sulphoxide or the like may be used. The elimination reaction is most preferably carried out in benzene or toluene by using DBN or DBU as a base at a temperature of 80° to 120° C.

b. A compound of the formula (III) is reacted with a reagent of the formula F—Y in a solvent at a temperature between −80° C. and 50° C., preferably at −78° C. to give a substance of the formula (II). It is preferably to use solvents such as halogenated hydrocarbons, e.g. dichloromethane, chloroform or the like, or aromatic solvents, such as benzene, toluene or the like; or alcohols, such as methanol, ethanol or the like. The reaction is accomplished in the presence of or without an inorganic base, preferably an alkali carbonate, such as sodium carbonate, potassium carbonate or the like; or in the presence of or without an alkali hydrogen carbonate, such as sodium hydrogen carbonate. The most preferred embodiment of the above reaction comprises reacting a compound of the formula (III) with phenylselenyl chloride—wherein in the formula F—Y, F means $C_6H_5$—Se— and Y stands for chlorine—in dichloromethane at a temperature between $-60°$ C. and $-80°$ C. without using any base. Subsequently, the resulting compound of the formula (III) is transformed to the desired product of the formula (I) by the means of the well-known oxidation-elimination reaction sequence (D.L.J. Clive: Tetrahedron, 34, 1949 (1978); H. J. Reich: Accts. Chem. Res., 12, 22 (1979)). In this sequence inorganic peroxides, such as hydrogen peroxide, metaperiodic acid and sodium metaperiodate, or organic peroxides, such as peroxyacetic acid, metachloroperbenzoic acid or tertiary-butyl hydroperoxide are preferably used as oxidizing agents. As solvents inorganic liquids, such as water, or organic solvents, preferably halogenated hydrocarbons, such as dichloroemethane and chloroform or alcohols, such as methanol and ethanol, or ether-type solvents, e.g. ethyl ether or the like, or the mixtures of the above solvents are used. The oxidation-elimination reaction is accomplished at a temperature of $-40°$ C. to $50°$ C., preferably from $0°$ to $25°$ C. in the presence of or without an inorganic base, such as preferably an alkali carbonate, e.g. sodium carbonate; or in the presence of or without an alkali hydrogen carbonate, e.g. sodium hydrogen carbonate. Presumably, the oxidation reaction results in the appropriate, selenoxide derivative under the conditions described above. However, this substance cannot be detected as it is immediately transformed to the compound of the formula (I) under the given reaction circumstances. This observation is in agreement with the literature data.

The oxidation-elimination step is most preferably carried out by using sodium metaperiodate in the presence of sodium hydrogen carbonate in a mixture of water with methanol at a temperature between $0°$ C. and $25°$ C.

The $PGF_{2\alpha}$ analogs of the formula (III) used as starting materials in the processes (a) and (b) can be prepared by using processes known in the literature (See e.g. M.P.L. Caton: Tetrahedron 35, 2705 81979) and the references cited therein).

c. A lactone of the formula (V) is reacted with a furan derivative of the formula (VI) in a solvent, preferably in an ether-type solvent, such as diethyl ether and tetrahydrofuran, or in an aprotic polar solvent, such as hexamethylphosphoric triamide; or in a mixture thereof, in the presence of a base such as preferably an alkyllithium, e.g. n-butyl or tertiary-butyllithium; or in the presence of an alkali hydride, such as sodium hydride and dimesyl sodium; or a lithium alkyl amide, such as lithium diisopropylamide or lithium dicyclohexylamide at a temperature between $-80°$ C. and $25°$ C., preferably at $-78°$ C. One to three equivalents of a base are used for this reaction. The most preferred embodiment of this reaction comprises using one equivalent of n-butyl lithium in tetrahydrofuran at $-78°$ C.

The resulting ketone derivative of the formula (IV) is heated at a temperature between $50°$ C. and $200°$ C., preferably at $70°$ to $90°$ C. in an organic solvent, preferably in an aromatic solvent, such as benzene, toluene or xylene; or a chlorinated solvent, such as dichloromethane, chloroform or dichloroethane, or without any solvent in the presence of an organic acid catalyst, preferably of an aromatic sulphonic acid, e.g. p-toluenesulphonic acid, or in the presence of a salt formed from an aromatic sulphonic acid with an organic base, such as pyridinium tosylate. The water formed during the reaction is removed by using water-trapping equipment. This process results in the analogues of interfuranyleneprostacyclin derivatives of the formula (I). The most preferred embodiment of this reaction comprises carrying out the reaction in benzene, in the presence of pyridinium tosylate as catalyst at a temperature between $70°$ to $90°$ C.

The lactones of the formula (V) used as starting materials in the method (c) are known from the literature (see e.g. R. A. Johnson and E. G. Nidy: J. Org. Chem. 45, 3802 (198)) or can be prepared analogously to known methods.

The $R^1$ and $R^2$ protecting groups can optionally be removed from the compounds of the formula (I) arising from the process (a), (b) or (c) by using methods known in the literature. Optionally, the salts of the formula (I) may also be prepared.

The stability of the compounds of the formula (I) of the invention prepared by using the above-described methods was compared to the stability of the sodium salt of $PGI_2$. This latter compound is rather unstable with a half-life of 3 to 4 minutes at a pH value of 7.4. The free acid ($PGI_2$) can even not be prepared because of its greater instability (R. A. Johnson et al.: J. Am. Chem. Soc. 100, 7690; 1978). The stability of the compounds of formula (I) of the invention is significantly higher. One of these, namely $2',5'$-interfuranylene-2,3,4-trinor-5,9$\alpha$-epoxy-9-deoxy-5,6-didehydro-$PGF_{1\alpha}$ can be stored in the form of the free acid at a pH value of 7.4 without any remarkable decomposition for 12 hours. This compound can be stored at $-20°$ C. with a decomposition of less than 10% for at least one month. The half-life of $2',5'$-interfuranylene-2,3,4-trinor-5,9$\alpha$-epoxy-9-deoxy-5,6-didehydro-16,17,18,19,20-pentanor-15-cyclopentyl-$PGF_{1\alpha}$ is about 3 hours at pH 3.

One of the pharmacologically most active representatives of the compounds of the invention is $2',5'$-interfuranylene-2,3,4-trinor-5,9$\alpha$-epoxy-9-deoxy-5,6-didehydro-$PGF_{1\alpha}$, the action of which is characterized by the following data:

1 Inhibition of the aggregation induced by 2 $\mu$moles of ADP in a platelet-rich plasma: ($ID_{50}=20$ ng/ml (human PRP); $ID_{50}=350$ ng/ml (rabbit PRP)).

Further compounds of the invention inhibit the aggregation induced by ADP in platelet-rich human plasma with the following $ID_{50}$ values:

$2',5'$-Interfuranylene-2,3,4-trinor-5,9$\alpha$-epoxy-9-deoxy-5,6-didehydro-16,17,18,19,20-pentanor-15-cyclopentyl-$PGF_{1\alpha}$: 35 ng/ml;

$2',5'$-Interfuranylene-2,3,4-trinor-5,9$\alpha$-epoxy-9-deoxy-5,6,13,14-tetradehydro-20-methyl-$PGF_{1\alpha}$: 40 ng/ml.

2. Hypotensive action induced in anaesthetized cat by intravenous bolus administration: $ED_{50}=14$ $\mu$g/kg of body-weight.

Both the platelet aggregation inhibiting as well as the hypotensive properties appear at a concentration higher by an order of magnitude than the corresponding effects of the reference $PGI_2$.

In addition, the compounds of the invention possess a wide-ranging (broad spectrum) cytoprotective activity both in the myocardium and gastrointestinal tract as well as against to liver damages. Further on, the compounds of the invention show other pharmacodynamic activities; namely, a relaxing effect on the guinea pig trachea and an inhibiting effect of tumor metastases induced in rats.

According to the pharmacological profile described above, the compounds of the invention can effectively be used alone or in combination with heparin for inhibiting the platelet aggregation without any platelet loss in extracorporeal circulations (such as e.g. kidney haemodialysis, heart-lung-apparatus and the like). The compound of the invention can also be used for the prevention or therapy of peripheral vascular diseases (atherosclerosis obliterans, Bürger disease, diabetic angiopathy, Raynaud disease).

The dimension of the segments affected by the myocardial infarction as well as the lethality are diminished by the compounds of the invention. The number and intensity (severity) of the anginal attacks are decreased in several types of the anginal diseases. On the basis of their bronchodilating effect, the compounds of the invention can advantageously be used for the diminition of the number (frequency) of asthma attacks. Further on, these compounds can preferably be employed in the therapy of ulcer diseases as a result of their gastrointestinal cytoprotective action. In addition, the spreading of tumours (after surgical operations) can be prevented by using the compounds of the invention.

An advantage in the therapy carried out with the compositions of the invention consists in that they can be administered by a gastrointestinal route, e.g. orally, in addition to the intravenous, subcutaneous and intramuscular routes. The suitable dose of the compounds of the invention is from 1 ng/kg of body-weight to 10 ng/kg of body-weight. The appropriate dose depends on the alteration to be treated, the severity of the disease, the rate of arriving of the medicament to the site of action as well as on the individual sensitivity of the patient or the organ needing the treatment and on the reactivity of the patient. The appropriate (suitable) doses and the most suitable route of administration can easily be determined by one skilled in the art.

For the preparation of the pharmaceutical compositions, the commonly used filling, diluting, aromatizing, formulation promoting, pH- and osmotic pressure-adjusting, stabilizing and absorption-promoting agents may be used. The pharmaceutical compositions can be solid (e.g. tablets, capsules, dragées, pilules etc.), liquids (e.g. drops, syrups etc.) or semi-liquid (creams, ointments, balsams, suppositories etc.).

The compounds of the invention may be used as single active ingredients or in the combination with other drugs in the pharmaceutical compositions.

The invention is illustrated in detail by aid of the following non-limiting Examples.

EXAMPLE 1

Preparation of 2′,5′-interfuranylene-2,3,4-trinor-5,9α-epoxy-9-deoxy-6-phenylselenyl-PGF$_{1α}$ methyl ester (compound of the formula (IIb), wherein X=Ph—Se—, R$^1$=methyl, R$^2$=hydrogen, R$^3$=—(CH$_2$)$_4$CH$_3$, A=trans—CH=CH— and B=valence bond)

To the suspension of 700 mg of sodium hydrogen carbonate in 100 ml of dichloromethane containing 2.7 g (6.88 mmoles) of 2′,5′-interfuranylene-2,3,4-trinor-PGF$_{2α}$ methyl ester (compound of the formula (III), wherein R$^1$=methyl, R$^2$=hydrogen, A=trans—CH= CH—, R$^3$=n—C$_5$H$_{11}$— and B=valence bond), a solution of 1.63 g (8.26 mmoles) of phenylselenyl chloride in 30 ml of dichloromethane are added dropwise at −78° C. within 10 minutes. The reaction proceeds during 90 minutes. Thereafter, 500 ml of ether are added to the reaction mixture and the resulting yellow solution is successively washed with 50 ml of saturated sodium hydrogen carbonate solution, 100 ml of water, 100 ml of saturated sodium chloride solution and dried over anhydrous magnesium sulphate. The crude product is subjected to chromatography on a short column (100 g of Kieselgel G, with a gradient elution from hexane/acetone 2:1 to hexane/acetone 1:1) to give 1450 mg of the named product as yellowish-white crystals, m.p.: 86°–88° C., R$_f$=0.45 (ethyl acetate); UV (C$_2$H$_5$OH): $\lambda_{max}$=260 nm, log $\epsilon$=4.210.

EXAMPLE 2

Preparation of 2′,5′-interfuranylene-2,3,4-trinor-5,9α-epoxy-9-deoxy-5,6-didehydro-PGF$_{1α}$ methyl ester (compound of the formula (I), wherein R$^1$=methyl, R$^2$=hydrogen, R$^3$=—(CH$_2$)$_4$CH$_3$, A=trans—CH=CH— and B=valence bond)

One ml of a saturated sodium hydrogen carbonate solution is added to a solution containing 1400 mg (2.56 mmoles) of 2′,5′-interfuranylene-2,3,4-trinor-5,9-epoxy-9-deoxy-6-phenylselenyl-PGF$_{1α}$ methyl ester (compound of the formula (II), wherein R$^1$=methyl, R$^2$=hydrogen, R$^3$=—(CH$_2$)$_4$CH$_3$, A=trans—CH= CH—, B=valence bond and X=Ph—Se—) in 50 ml of methanol and 820 mg (3.84 mmoles) of sodium metaperiodate are portionwise added at 0° C. The mixture is stirred at 0° C. for one hour, then at room temperature for 4 hours. The mixture is filtered by suction and the precipitate is washed twice with 10 ml of ethyl acetate each. To the filtrate 400 ml of ethyl acetate are added and it is successively extracted with 50 ml of water, 50 ml of saturated sodium chloride solution and dried over anhydrous magnesium sulphate in the presence of triethylamine. After removing the solvent, the resulting material is purified by using a short-column chromatography (200 g of Kieselgel G, with a gradient elution from hexane/acetone 2:1 to hexane/acetone 1:1) to give 425 mg of the named product as yellowish-white crystals, m.p.: 114°–117° C., R$_f$=0.62 (hexane-acetone 1:1); UV (C$_2$H$_5$OH) $\lambda_{max}$=326 nm, log $\epsilon$=3.93 and 301 nm, log $\epsilon$=4.14.

EXAMPLE 3

Preparation of 2′,5′-interfuranylene-2,3,4-trinor-5,9α-epoxy-9-deoxy-5,6-didehydro-PGF$_{1α}$ (compound of the formula (I), wherein R$^1$=hydrogen, R$^2$=hydrogen, R$^3$=—(CH$_2$)$_4$CH$_3$, A=trans—CH=CH— and B=valence bond)

Five ml (5 mmoles) of an aqueous 1M sodium hydroxide solution are added to a solution containing 400 mg (1.02 mmoles) of 2′,5′-interfuranylene-2,3,4-trinor-5,9α-epoxy-9-deoxy-5,6-didehydro-PGF$_{1α}$ methyl ester (compound of the formula (I), wherein R$^1$=methyl, R$^2$=hydrogen, R$^3$=—(CH$_2$)$_4$CH$_3$, A=trans—CH= CH— and B=valence bond) in 10 mol of methanol of the mixture is stirred at room temperature for 3 hours. The methanol is removed without heating under reduced pressure and the residue is extracted with solvents cooled to 520 C. First 25 ml of ether and 30 ml of water are added and the ethereal phase is separated. The aqueous phase is repeatedly washed with 20 ml of ether, then acidified to a pH of 3 to 4 by using about 8 ml of aqueous sodium hydrogen sulphate solution. The aqueous layer is extracted twice with 25 ml of ether each, the organic phases are combined and washed twice with 10 ml of saturated sodium chloride solution each and dried over anhydrous magnesium sulphate to give after evaporation 292 mg of the pure named product as yellowish-white crystals, m.p.: 108°–110° C., $R_f=0.30$ (benzene/dioxane/acetic acid 20:10:1); UV ($C_2H_5OH$): $\lambda_{max}$ 295 nm, log $\epsilon=4.16$ and $\lambda_{max}=235$ nm, log $\epsilon=3.93$.

EXAMPLE 4

Preparation of
2′,5′-interfuranylene-2,3,4-trinor-5,9α-epoxy-9-deoxy-6-iodo-PGF$_{1\alpha}$ methyl ester (compound of the formula (IIa), wherein $R^1$=methyl, $R^2$=hydrogen, $R^3$=—(CH$_2$)$_4$CH$_3$, A=trans—CH=CH—, B=valence bond and X=iodine)

Ten ml of a saturated sodium hydrogen carbonate solution are added to a solution containing 528 mg (1.40 mmoles) or 2′,5′-interfuranylene-2,3,4-trinor-PGF$_{2\alpha}$ methyl ester /compound of the formula (III), wherein $R^1$=methyl, $R^2$=hydrogen, $R^3$=—(CH$_2$)$_4$CH$_3$, A=-trans—CH=CH— and B=valence bond) in 20 ml of dichloromethane and 310 mg (1.22 mmoles) of iodine are portionwise added at 0° C. under vigorous stirring. After one hour 10 ml of sodium thiosulphate solution are added to the reaction mixture, the whole is stirred for additional 15 minutes, whereupon 100 ml of ethyl acetate are added. The organic layer is successively extracted with 10 ml of sodium thiosulphate solution, 10 ml of water and 10 ml of saturated sodium chloride solution and dried over anhydrous magnesium sulphate. The reaction mixture is purified by short-column chromatography (by using 50 g of Kieselgel G, with a gradient elution from hexane/acetone 2:1 to hexane/acetone 4:3) to give 280 mg of the named product as a yellow oil, $R_f=0.64$; (acetone/hexane 2:1); UV ($C_2H_5OH$): $\lambda_{max}=256$ nm, log $\epsilon=4.25$.

EXAMPLE 5

Preparation of
2′,5′-interfuranylene-2,3,4-trinor-5,9α-epoxy-9-deoxy-5,6-didehydro-PGF$_{1\alpha}$ methyl ester (compound of the formula (I), wherein $R^1$=methyl, $R^2$=hydrogen, $R^3$=—(CH$_2$)$_4$CH$_3$, A=trans—CH=CH— and B=valence bond)

Three ml of diazabicycloundecene (DBU) are added to a solution containing 823 mg (1.63 mmoles) of 2′,5′-interfuranylene-2,3,4-trinor-5,9α-epoxy-9-deoxy-6-iodo-PGF$_{1\alpha}$ methyl ester (compound of the formula (IIa) wherein $R^1$=methyl, $R^2$=hydrogen, $R^3$=—(CH$_2$)$_4$CH$_3$, A=trans—CH=CH—, B=valence bond and X=iodine) in 10 ml of toluene, the mixture is stirred at 60° C. for 3 hours and at room temperature overnight. Then the mixture is diluted by adding 100 ml of cold ethyl acetate, extracted twice with 10 ml of cold sodium hydrogen sulphate solution each, then with 10 ml of water and 10 ml of saturated sodium chloride solution and dried over anhydrous magnesium sulphate in the presence of triethylamine. After purifying by short-column chromatography (100 g of Kieselgel G and ethyl acetate containing 1% triethylamine as eluant), 362 mg of the desired product are obtained, the physical properties of which are identical with those of the product described in Example 2.

EXAMPLE 6

Preparation of
11,15-bis(tetrahydropyranyl)-2′,5′-interfuranylene-2,3,4-trinor-5-oxo-PGF$_{1\alpha}$ methyl ester (compound of the formula (IV) wherein $R^1$=methyl, $R^2$=tetrahydropyranyl, $R^3$=—(CH$_2$)$_4$CH$_3$, $R^4$=hydrogen, A=trans—CH=CH— and B=valence bond)

A 2M solution of n-butyllithium (2.2 ml; 4.4 mmoles) in hexane are added dropwise to a solution containing 300 mg (2.67 mmoles) of 2-furancarboxylic acid (compound of the formula (VI), wherein $R^1$=hydrogen) in 25 ml of tetrahydrofuran at −78° C. and the mixture is stirred at the same temperature for 40 minutes. Thereafter, a solution containing 303 mg (0.68 mmoles) of 3-oxo-7β-(3′-tetrahydropyranyloxy-1′-octene-1′-yl)-8α-tetrahydropyranyloxy-2-oxabicyclo[4.3.0]nonane (compound of the formula (V), wherein $R^2$=tetrahydropyranyl, $R^3$=—(CH$_2$)$_4$CH$_3$, A=trans—CH=CH—, and B=valence bond) in 14 ml of tetrahydrofuran is added dropwise at −78° C. The mixture is stirred at the same temperature for 30 minutes, whereupon the temperature is gradually increased to 0° C. and the reaction is stopped by adding 20 ml of water. After adding 40 ml of ether, the organic phase is washed with 20 ml of 0.1N sodium hydroxide solution and then with 20 ml of water. The combined aqueous phase is acidified to pH 3 to 4 by adding 20 ml of sodium hydrogen sulphate solution, washed twice with 40 ml of ether each of the organic phases are combined. After washing with 10 ml of water and 10 ml of saturated sodium chloride solution, 10 ml of etheral diazomethane solution are added to the organic solution at 0° C., the mixture is stirred for 5 minutes and dried over anhydrous magnesium sulphate. After purifying by chromatography on a short column (25 g of Kieselgel G and 2:1 mixture of hexane/ethyl acetate as eluant), 69 mg of the named product are obtained as a colorless oil, $R_f=0.40$ (hexane/ethyl acetate 1:1); UV ($C_2H_5OH$): $\lambda_{max}=256$ nm, log = 4.200.

EXAMPLE 7

Preparation of
2′,5′-interfuranylene-2,3,4-trinor-5,9α-epoxy-9-deoxy-5-methoxy-PGF$_{1\alpha}$ methyl ester (compound of the formula (IV) wherein $R^1$=methyl, $R^2$=hydrogen, $R^3$=—(CH$_2$)$_4$CH$_3$, $R^4$=methyl, A=trans—CH=CH— and B=valence bond)

A solution containing 328 mg (0.58 mmole) of 11,15-bis(tetrahydropyranyl)-2′,5′-interfuranylene-2,3,4-trinor-5-oxo-PGF$_{1\alpha}$ methyl ester (compound of the formula (IV), wherein $R^1$=methyl, $R^2$=tetrahydropyranyl, $R^3$=—(CH$_2$)$_4$CH$_3$, $R^4$=hydrogen, A=trans—CH=CH— and B=valence bond) and catalytic amount of pyridinium tosylate in 5 ml of methanol is stirred overnight, then 50 ml of ethyl acetate are added. The mixture is successively washed with 8 ml of water, 8 ml of saturated sodium chloride solution and then dried over anhydrous magnesium sulphate in the presence of triethylamine. After purifying by chromatography on a short column (20 g of Kieselgel G and an 1:1 mixture of hexane/acetone as eluant), 197 mg of the title product are obtained as a colorless oil.

According to the thin layer chromatography, this substance is a mixture of two isomers, with the $R_f$ values of 0.33 and 0.27, respectively by using an 1:1 mixture of hexane/acetone as developing agent.

EXAMPLE 8

Preparation of
11,15-diacetyl-2',5'-interfuranylene-2,3,4,-trinor-5,9α-epoxy-9-deoxy-5-methoxy-PGF$_{1α}$ methylester (compound of the formula (IV), wherein R$^1$=methyl, R$^2$=acetyl, R$^3$=—(CH$_2$)$_4$CH$_3$, R$^4$=methyl, A=trans—CH═CH— and B=valence bond)

One ml of triethylamine and 0.2 ml (2.12 mmoles) of acetic anhydride are added to a solution containing 183 mg (0.43 mmole) of 2',5'-interfuranylene-2,3,4-trinor-5,9α-epoxy-9 -deoxy-5-methoxy-PGF$_{1α}$ methyl ester (compound of the formula (IV), wherein R$^1$=methyl, R$^2$=hydrogen, R$^3$=—(CH$_2$)$_4$CH$_3$, R$^4$=methyl, A=-trans—CH═CH— and B=valence bond) in 10 ml of dichloromethane. The solution is kept at room temperature overnight, whereupon 5 ml of water are added and the mixture is vigorously stirred for 15 minutes. After adding 50 ml of ethyl acetate, the organic layer is successively washed with 10 ml of sodium hydrogen sulphate solution, 10 ml of water, 10 ml of saturated sodium hydrogen carbonate solution, 10 ml of water, 10 ml of saturated sodium chloride solution and dried over anhydrous magnesium sulphate. After evaporation 193 mg of the named product are obtained, which can be processed further without purification. Rf=0.21 (hexane/ethyl acetate 2:1).

EXAMPLE 9

Preparation of
11,15-diacetyl-2',5'interfuranylene-2,3,4-trinor-5,9α-epoxy-9-deoxy-5,6-didehydro-PGF$_{1α}$ methyl ester (compound of the formula (I), wherein R$^1$=methyl, R$^2$=acetyl, R$^3$=—(CH$_2$)$_4$CH$_3$, A=trans—CH═CH— and B=valence bond)

Five mg (0.02 mmole) of pyridinium tosylate are added to a solution containing 138 mg (0.27 mmole) of 11,15-diacetyl-2',5'-interfuranylene-2,3,4-trinor-5,9α-epoxy-9-deoxy-5-methoxy-PGF$_{1α}$ methyl ester (compound of the formula (IV), wherein R$^1$=methyl, R$^2$=acetyl, R$^3$=—(CH$_2$)$_4$CH$_3$, R$^4$=methyl, A=trans—CH═CH— and B=valence bond) in 15 ml of benzene and the mixture is boiled for 30 minutes under reflux while removing the water formed. Then 1 mol of triethylamine is added to the mixture and it is purified by chromatography on a short column (20 g Kieselgel G and a 2:1 mixture of hexane/ethyl acetate as eluant). The title product is obtained as a colorless oil in a yield of 53 g, R$_f$=0.28 (hexane/ethyl acetate 2:1); UV (C$_2$H$_5$OH): $\lambda_{max}$=237 nm, log $\epsilon$=3.97 and $\lambda_{max}$=302 nm, log $\epsilon$=4.16.

EXAMPLE 10

Preparation of
2',5'-interfuranylene-2,3,4-trinor-5,9α-epoxy-9-deoxy-5,6-didehydro-PGF$_{1α}$ (compound of the formula (I), wherein R$^1$=hydrogen, R$^2$=hydrogen, R$^3$=—(CH$_2$)$_4$CH$_3$, A=trans—CH═CH— and B=valence bond)

A solution containing 105 mg (0.22 mmole) of 11,15-diacetyl-2',5'-interfuranylene-2,3,4-trinor-5,9α-epoxy-9-deoxy-5,6-didehydro-PGF$_{1α}$ methyl ester (compound of the formula (I) wherein R$^1$=methyl, R$^2$=acetyl, R$^3$=—(CH$_2$)$_4$CH$_3$, A=trans—CH═CH— and B=valence bond) and 1 ml (1 mmole) of 1M aqueous sodium hydroxide solution in 5 ml of methanol is kept at room temperature for 2 days. Then the methanol is removed at room temperature under reduced pressure and 20 ml ether as well as 20 ml of water are added to the residue. The aqueous phase is again washed with 10 ml of ether and acidified to a pH of 3 to 4 by adding about 1.2 ml of sodium hydrogen sulphate solution. The aqueous layer is extracted twice with 25 ml of ether each, the etheral phases are combined and washed twice with 5 ml of saturated sodium chloride solution each and dried over anhydrous magnesium sulphate. After evaporation, 13 mg of the named product are obtained which does not require any further purification. The physical characteristics of the substance are identical with those of the product described in the Example 3.

EXAMPLE 11

Preparation of
2',5'-interfuranylene-2,3,4-trinor-5,9α-epoxy-9-deoxy-5,6-didehydro-PGF$_{1α}$ methyl ester (compound of the formula (I), wherein R$^1$=methyl, R$^2$=hydrogen, R$^3$=—(CH$_2$)$_4$CH$_3$, A=trans—CH═CH— and B=valence bond)

A solution containing 94 g (0.20 mmole) of 11,15-diacetyl-2',5'-interfuranylene-2,3,4-trinor-5,9α-epoxy-9-deoxy-5,6-didehydro-PGF$_{1α}$ methyl ester (compound of the formula (I), wherein R$^1$=methyl, R$^2$=acetyl, R$^3$=—(CH$_2$)$_4$CH$_3$, A=trans—CH═CH— and B=valence bond) and 1 ml (1 mmole) of an 1M methanolic sodium methoxide solution in 3 ml of methanol is stirred at room temperature for 3 hours. After adding 50 ml of ether, the mixture is washed with 8 ml of cold water, twiche with 8 ml of saturated sodium chloride solution each and dried over anhydrous magnesium sulphate. After purifying by chromatography on a short column (10 g of Kieselgel G and a 2:1 mixture of hexane/acetone as eluant), 63 g of the named product are isolated which is compeletly identical with the substance described in Example 2.

EXAMPLE 12

Preparation of
2',5'-interfuranylene-2,3,4-trinor-5,9α-epoxy-9-deoxy-6-bromo-PGF$_{1α}$ methyl ester (compound of the formula (IIa), wherein R$^1$=methyl, R$^2$=hydrogen, R$^3$=—(CH$_2$)$_4$CH$_3$, A=trans—CH═CH—, B=valence bond and X=bromine)

Sixty mg (0.33 mmole) of N-bromosuccinimide are added to a solution containing 87 mg (0.2 mmole) of 2',5'-interfuranylene-2,3,4trinor-PGF$_{2α}$ methyl ester (compound of the formula (III), wherein R$^1$=methyl, R$^2$=hydrogen, R$^3$=—(CH$_2$)$_4$CH$_3$, A=trans—CH═CH— and B=valence bond) in 3 ml of dichloromethane and the mixture is stirred at room temperature for 3 hours. The reaction mixture is subjected without any previous purification to chromatography on a short column (20 g of Kieselgel G and an 1:1 mixture of dichloromethane/acetone) to give 50 mg of the named product, R$_f$=0.23 (hexane/acetone 1:1); UV (C$_2$H$_5$OH): $\lambda_{max}$=258 nm, log $\epsilon$=4.18.

EXAMPLE 13

Preparation of
2',5'-interfuranylene-2,3,4-trinor-5,9α-epoxy-9-deoxy-6-phenylselenyl-16,17,18,19,20-pentanor-15-cyclopentyl-PGF$_{1α}$ methyl ester (compound of the formula (II), wherein R$^1$=methyl, R$^2$=hydrogen, R$^3$=cyclopentyl, A=trans—CH=CH—, B=valence bond and X=C$_6$H$_5$—Se—group)

After suspending 2.798 g of sodium hydrogen carbonate in a solution containing 2.60 g (6.66 mmoles) of 2',5'-interfuranylene-2,3,4-trinor-PGF$_{2α}$ methyl ester (compound of the formula (III), wherein R$^1$=methyl, R$^2$=hydrogen, A=—CH=CH—, R$^3$=cyclopentyl and B=valence bond) in 100 ml of dichloromethane 1.912 g (9.99 mmoles) of phenylselenyl chloride dissolved in 30 ml of dichloromethane are added dropwise to the former solution at −78° C. within 30 minutes. The mixture is stirred for 30 minutes, then 5 ml of triethylamine are added and the solution it let warm to room temperature. After adding 500 ml of ether, it is successively washed with 70 ml of water and 70 ml of saturated sodium chloride solution. After purifying by chromatography on a short column (250 g of Kieselgel G and a gradient elution from 2:1 hexane/acetone mixture to an 1:1 hexane/acetone mixture), 1.150 g of the named product are obtained as white crystals, m.p.: 153°–154° C., R$_f$=0.33 (ethyl acetate); UV (C$_2$H$_5$OH): λ$_{max}$=260 nm, log ϵ=4.205.

EXAMPLE 14

Preparation of
2',5'-interfuranylene-2,3,4-trinor-5,9α-epoxy-9-deoxy-5,6-didehydro-16,17,18,19,20-pentanor-15-cyclopentyl-PGF$_{1α}$ methyl ester (compound of the formula (I), wherein R$^1$=methyl, R$^2$=hydrogen, R$^3$=cyclopentyl, A=trans—CH=CH— and B=valence bond)

Three ml of a saturated sodium hydrogen carbonate solution and 647 (3.02 mmoles) of sodium metaperiodate are added to a solution containing 1.1 g (2.02 mmoles) of 2',5'-interfuranylene-2,3,4-trinor-5,9α-epoxy-9-deoxy-6-phenylselenyl-16,17,18,19,20-pentanor-15-cyclopentyl-PGF$_{1α}$ methyl ester (the product described in the preceeding Example) in 50 ml of methanol cooled to 0° C. After stirring at 0° C. for 30 minutes and at 25° C. for 3 hours, the reaction mixture is filtered by suction, the precipitate is washed twice with 5 ml of methanol each and the filtrate is evaporated nearly completely under reduced pressure. The residue is diluted with 200 ml of ethyl acetate, extracted with 20 ml of water and then with 20 ml of a saturated sodium chloride solution and finally dried over anhydrous magnesium sulphate in the presence of triethylamine. After purification by chromatography on a short column (100 g of Kieselgel G and 2:1 mixture of hexane/acetone containing 1% of triethylamine as eluant/, 298 mg of the named product are obtained as a yellowish crystalline substance, m.p.: 131°–134° C., R$_f$=0.27 (hexane/acetone 3:2).

EXAMPLE 15

Preparation of
2',5'-interfuranylene-2,3,4-trinor-5,9α-epoxy-9-deoxy-5,6-didehydro-16,17,18,19,20-pentanor-15-cyclopentyl-PGF$_{1α}$ (compound of the formula (I), wherein R$^1$=hydrogen, R$^2$=hydrogen, R$^3$=cyclopentyl, A=trans—CH=CH— and B=valence bond)

A solution containing 250 ml (0.64 mmole) of 2',5'-interfuranylene-2,3,4-trinor-5,9α-epoxy-9-deoxy-5,6-didehydro-16,17,18,19,20-pentanor-15-cyclopentyl-PGF$_{1α}$ methyl ester (the product described in the preceding Example) and 5 ml (5 mmoles) of an 1M aqueous sodium hydroxide solution in 15 ml of methanol is kept at room temperature for 3 hours, then evaporated approximately to its half volume, then the mixture is purified by cooled solvents according to the following. It is diluted with 25 ml of water and 25 ml of ether and the aqueous phase is acidified to a pH value of 3 to 4 by adding an 1M sodium hydrogen sulphate solution. The precipitated white material is dissolved in 50 ml of ethyl acetate and the two phases are separated. The aqueous phase is again washed with 20 ml of ethyl acetate, the ethyl acetate phases are combined, washed twice with 10 ml of a saturated sodium chloride solution each and dried over anhydrous magnesium sulphate. After evaporation, 199 mg of the named product are obtained in the form of white crystals, m.p.: 157°–160° C., R$_f$=0.28 (benzene/dioxane/acetic acid 20:10:1).

EXAMPLE 16

Preparation of
2',5'-interfuranylene-2,3,4-trinor-5,9α-epoxy-9-deoxy-5,6-didehydro-16,17,18,19,20-pentanor-15-cyclopentyl-PGF$_{1α}$ calcium salt (compound of the formula (I), wherein R$^1$=Ca$_{\frac{1}{2}}$, R$^2$=hydrogen, R$^3$=cyclopentyl, A=trans—CH=CH—, B=valence bond) A solution containing 176 mg (0.45 mmole) of 2',5'-interfuranylene-2,3,4-trinor-5,9α-epoxy-9-deoxy-5,6-didehydro-16,17,18,19,20-pentanor-15-cyclopentyl-PGF$_{1α}$ methyl ester and 5 ml of an 1N sodium hydroxide solution in 10 ml of methanol is stirred at room temperature for 90 minutes, then methanol is removed under reduced pressure. After adding 10 ml of water to the residue and washing with 25 ml of ether, the aqueous phase is acidified to a pH value of 4 by adding about 5 ml of an 1M sodium hydrogen sulphate solution and extracted as cold 3 times with 30 ml of ethyl acetate each. The combined ethyl acetate solution is washed with 10 ml of saturated sodium chloride solution. After evaporation, the residue is dissolved in 10 ml of tetrahidrofuran and after adding 3 ml of water, 30 mg (0.53 mmole) of calcium oxide are added. The resulting turbid solution is stirred overnight, then filtered, the filtrate is evaporated to dryness and after adding benzene it is again evaporated to dryness. The evaporation residue is stirred with 20 ml of ethanol for 20 minutes and filtered. After evaporating the filtrate, the named product is obtained as a pure substance as white crystals, m.p.: 150°–155° C. (with decomposition), R$_f$=0.28 (benzene/dioxane/acetic acid 20:10:1).

The calcium content of the compound can be determined by conductometric titration by using an acid. In this case, the calcium content of a sample of 15 mg was found to be 0.785 mg.

EXAMPLE 17

Preparation of 2′,5′-interfuranylene-2,3,4-trinor-5,9α-epoxy-9-deoxy-6-phenylselenyl-13,14-didehydro-20-methyl-PGF$_{1α}$ methyl ester (compound of the formula (II), wherein R$^1$=methyl, R$^2$=hydrogen, R$^3$=n—C$_5$H$_{11}$—, A=—C≡C—, B=—CHR$^5$, R$^5$=hydrogen and Y=C$_6$H$_5$—Se—group)

After adding 194 mg (2.31 mmoles) of sodium hydrogen carbonate to a solution containing 780 mg (1.93 mmoles) of 2′,5′-interfuranylene-2,3,4-trinor-13,14-didehydro-20-methyl-PGF$_{2α}$ methyl ester (compound of the formula (III), wherein R$^1$=methyl, R$^2$=hydrogen, R$^3$=n—C$_5$H$_{11}$—, A=—C≡C—, B=—CHR$^5$, and R$^5$=hydrogen) in 15 ml of dichloromethane, the solution is cooled to −78° C., 443 mg (2.31 mmoles) of phenylselenyl chloride dissolved in 5 ml of dichloromethane are added under stirring within 10 minutes and the mixture is stirred at −78° C. for one additional hour. After diluting with 50 ml of ethyl acetate, it is successively washed with 10 ml of a saturated sodium hydrogen carbonate solution, 20 ml of water, 20 ml of a saturated sodium chloride solution and dried over anhydrous magnesium sulphate. After purification by chromatography on a short column (70 g of Kieselgel G and a 2:1 mixture of ethyl acetate/hexane as eluant), 200 mg of the named product are obtained as a colorless oil, R$_f$=0.31 (ethyl acetate/hexane 2:1); UV (C$_2$H$_5$OH): λ$_{max}$ 259 nm, log ε=4.220.

EXAMPLE 18

Preparation of 2′,5′-interfuranylene-2,3,4-trinor-5,9α-epoxy-9-deoxy-5,6,13,14-tetradehydro-20-methyl-PGF$_{1α}$ methyl ester (compound of the formula (I), wherein R$^1$=methyl, R$^2$=hydrogen, R$^3$=n—C$_5$H$_{11}$—, A=—C≡C—, B=—CHR$^5$ and R$^5$=hydrogen)

143 mg (0.67 mmole) of sodium metaperiodate are given to a solution containing 250 mg (0.45 mmole) of 2′,5′-interfuranylene-2,3,4-trinor-5,9α-epoxy-9-deoxy-6-phenylselenyl-13,14-didehydro-20-methyl-PGF$_{1α}$ methyl ester (prepared as described in the preceding Example) and 0.5 ml of a saturated sodium hydrogen carbonate solution in 3 ml of methanol at 0° C. The mixture is stirred at 0° C. for 30 minutes and then at room temperature overnight. After filtration, the precipitate is washed with 5 ml of ethyl acetate. The filtrate is diluted with 10 ml of water and extracted twice with 20 ml of ethyl acetate each. The combined organic solution is washed twice with 5 ml of saturated sodium chloride solution each, then dried over anhydrous magnesium sulphate in the presence of triethylamine. After purification by chromatography on a short column (30 g of Kieselgel G and a 4:1 mixture of dichloromethane/acetone containing 1% of triethylamine as eluant), 24 mg of the named product are obtained as a colorless oil which becomes crystalline on standing, R$_f$=0.41 (dichloromethane/acetone 4:1), m.p.: 99°–100° C.

EXAMPLE 19

Preparation of 2′,5′-interfuranylene-2,3,4-trinor-5,9α-epoxy-9-deoxy-5,6,13,14-tetradehydro-20-methyl-PGF$_{1α}$ (compound of the formula (I), wherein R$^1$=hydrogen, R$^2$=hydrogen, R$^3$=n—C$_5$H$_{11}$—, A=—C≡C—, B=—CHR$^5$ and R$^5$=hydrogen)

A solution containing 24 mg (0.06 mmole) of 2′,5′-interfuranylene-2,3,4-trinor-5,9α-epoxy-9-deoxy-5,6,13,14-tetradehydro-20-methyl-PGF$_1$ methyl ester (prepared as described in the preceding Example) and 0.3 ml (0.3 mmole) of an 1N aqueous sodium hydroxide solution in 3 ml of methanol is stirred at room temperature overnight. Then, methanol is evaporated under reduced pressure and the residue is diluted with 2 ml of water. The following operations are carried out under cooling by ice by using solvents at a temperature of 5° to 10° C. The mixture is acidified to a pH value of a 3 to 4 by adding an 1M sodium hydrogen sulphate solution then the precipitated substance is extracted twice with 10 ml of ethyl acetate each. After combining the ethyl acetate phases and washing twice with 3 ml of a saturated sodium chloride solution each, the organic solution is dried over anhydrous magnesium sulphate. After evaporating the solvent, 19 mg of the desired product are obtained as a colorless oil, R$_f$=0.46 (benzene/dioxane/acetic acid 20:10:1).

We claim:

1. A racemic or optically active interfuranylene-prostacyclin of the formula (I)

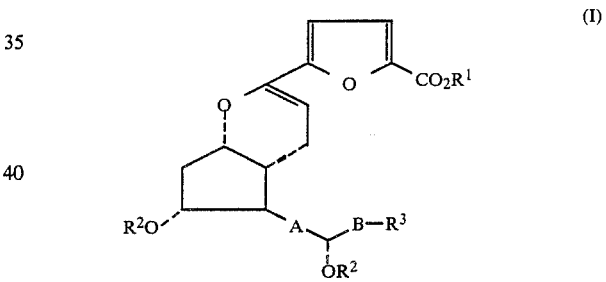

(I)

wherein
R$^1$ stands for hydrogen or a straight or branched chain C$_{1-6}$ alkyl group, a pharmaceutically acceptable inorganic cation or for the protonated form of a pharmaceutically acceptable base containing an amino group;
R$^2$ stands for hydrogen, a C$_{1-4}$ alkanoyl or benzoyl group, or a trialkylsilyl or an alkoxy-alkyl group;
R$^3$ stands for a straight or branched chain C$_{1-6}$ alkyl group, a phenyl group unsubstituted or substituted by halogen or by a C$_{1-4}$ alkyl group, or a cycloalkyl group;
A stands for an ethylene or for a cis- or trans-vinylene or —C≡C— group;
B means a chemical bond, a —CHR$^5$—, —CHR$^5$—CH$_2$— or a —CH$_2$—O— group; and
R$^5$ means hydrogen or a C$_{1-4}$ alkyl group.

2. 2′,5′-interfuranylene-2,3,4-trinor-5,9α-epoxy-9-deoxy-5,6-didehydro-PGF$_{1α}$ or the sodium salt thereof as defined in claim 1.

3. 2′,5′-interfuranylene-2,3,4-trinor-5,9α-epoxy-9-deoxy-5,6,13,14-tetradehydro-PGF$_{1α}$ as defined in claim 1.

4. 2',5'-interfuranylene-2,3,4-trinor-5,9α-epoxy-9-deoxy-5,6-didehydro-16,17,18,19,20-pentanor-15-cyclopentyl-PGF$_{1\alpha}$ as defined in claim 1.

5. 2',5'-interfuranylene-2,3,4-trinor-5,9α-epoxy-9-deoxy-5,6,13,14-tetradehydro-16,17,18,19,20-pentanor-15-cyclopentyl-PGF$_{1\alpha}$ as defined in claim 1.

6. 2',5'-interfuranylene-2,3,4-trinor-5,9α-epoxy-9-deoxy-5,6-didehydro-16,17,18,19,20-pentanor-15-cyclopentyl-PGF$_{1\alpha}$ methyl ester as defined in claim 1.

7. The compound of the Formula (I) defined in claim 1 selected from the group which consists of:
  2',5'-interfuranylene-2,3,4-trinor-5,9-alpha-epoxy-9-deoxy-5,6-didehydro-PGF$_{1\alpha}$;
  2',5'-interfuranylene-2,3,4-trinor-5,9-alpha-epoxy-9-deoxy-5,6-didehydro-16,17,18,19,20-pentanor-15-cyclopentyl-PGF$_{1\alpha}$; and
  2',5'-interfuranylene-2,3,4-trinor-5,9-alpha-epoxy-5,6,13,14-tetrahydro-20-methyl-PGF$_{1\alpha}$; or a pharmaceutically acceptable salt thereof.

8. 2',5'-interfuranylene-2,3,4-trinor-5,9α-epoxy-9-deoxy-5,6-didehydro-16,17,18,19,20-pentanor-15-cyclopentyl-PGF$_{1\alpha}$ calcium salt as defined in claim 1.

9. 2',5'-interfuranylene-2,3,4-trinor-5,9α-epoxy-9-deoxy-5,6,13,14-tetradehydro-20-methyl-PGF$_{1\alpha}$ methyl ester as defined in claim 1.

10. 2',5'-interfuranylene-2,3,4-trinor-5,9α-epoxy-9-deoxy-5,6,13,14-tetradehydro-20-methyl-PGF$_{1\alpha}$ as defined in claim 1.

11. A platelet aggregation inhibiting, antithrombotic, hypotensive and anti-atherosclerotic pharmaceutical composition, which comprises as active ingredient at least one racemic or optically active interfuranylene-prostacyclin as defined in claim 1, in admixture with the pharmaceutically acceptable filling, diluting, aromatizing, formulation-promoting, pH- and osmotic pressure-adjusting, stabilizing, and absorption-promoting and/or other pharmaceutically acceptable formulating additive materials.

* * * * *